(12) United States Patent
Numajiri

(10) Patent No.: US 8,831,783 B2
(45) Date of Patent: Sep. 9, 2014

(54) BIOCHEMICAL PROCESSING APPARATUS

(75) Inventor: Yasuyuki Numajiri, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 148 days.

(21) Appl. No.: 13/216,318

(22) Filed: Aug. 24, 2011

(65) Prior Publication Data

US 2011/0306033 A1    Dec. 15, 2011

Related U.S. Application Data

(62) Division of application No. 11/295,642, filed on Dec. 7, 2005, now Pat. No. 8,025,853.

(30) Foreign Application Priority Data

Dec. 13, 2004  (JP) .................................. 2004-359892

(51) Int. Cl.
*C12Q 3/00*   (2006.01)

(52) U.S. Cl.
USPC ........... 700/266; 422/503; 422/504; 422/505; 422/516; 422/517; 422/81; 422/82; 422/82.05; 422/82.06; 422/82.07; 422/82.08; 422/82.09; 422/82.1; 422/82.11; 422/68.1; 137/15.2

(58) Field of Classification Search
CPC .................................................... G01N 35/08
USPC ..................... 422/503–505, 516, 517, 81, 82, 422/82.05–82.11, 68.1; 137/15.2; 700/266
See application file for complete search history.

(56) References Cited

U.S. PATENT DOCUMENTS

| | | |
|---|---|---|
| 5,287,733 A | 2/1994 | Oku et al. |
| 5,445,934 A | 8/1995 | Fodor et al. |
| 5,922,591 A | 7/1999 | Anderson et al. |
| 6,100,541 A | 8/2000 | Nagle et al. |
| 2004/0223874 A1 | 11/2004 | Numajiri |
| 2005/0180880 A1 | 8/2005 | Itoh et al. |
| 2005/0284800 A1 | 12/2005 | Handa et al. |
| 2007/0071637 A1 | 3/2007 | Numajiri |

FOREIGN PATENT DOCUMENTS

| | | |
|---|---|---|
| JP | 02-040562 A | 2/1990 |
| JP | 04-131763 A | 5/1992 |
| JP | 05-306973 A | 11/1993 |
| JP | 10-232157 A | 9/1998 |
| JP | 11-509094 A | 8/1999 |
| JP | 11-304817 A | 11/1999 |
| JP | 2003-004753 A | 1/2003 |
| JP | 2004-301767 A | 10/2004 |
| JP | 2004-340702 A | 12/2004 |
| WO | 97/02357 A1 | 1/1997 |

OTHER PUBLICATIONS

A. Lueking, et al., "Protein Microarrays for Gene Expression and Antibody Screening", Analytical Biochemistry 270, pp. 103-111, 1999.
Japanese Office Action dated Oct. 21, 2009, in related Japanese Patent Appln. No. 2004-359892.

*Primary Examiner* — Shogo Sasaki
(74) *Attorney, Agent, or Firm* — Fitzpatrick, Cella, Harper & Scinto

(57) ABSTRACT

A biochemical processing apparatus is provided having a stage receiving a biochemical reaction cartridge which includes chambers and flow paths communicating therebetween, a moving system for moving liquid via the flow paths, and a detector for detecting the presence of the liquid in a chamber and/or the amount of the liquid. In addition, a determining device determines a result of the movement of the liquid from the information of the liquid in the chamber detected by the detector.

6 Claims, 6 Drawing Sheets

BIOCHEMICAL PROCESSING APPARATUS

This application is a divisional of application Ser. No. 11/295,642, filed on Dec. 7, 2005, now U.S. Pat. No. 8,025,853.

BACKGROUND OF THE INVENTION

1. Field of the Invention

The present invention relates to a biological technique for analyzing, for example, cell, microorganism, chromosome, nucleic acid and the like in a sample by utilizing a biochemical reaction, such as an antigen-antibody reaction or a nucleic acid hybridization reaction.

2. Description of the Related Art

Most of analyzers for analyzing samples such as blood use an immunological procedure utilizing an antigen-antibody reaction or a procedure utilizing nuclei acid hybridization. For example, protein such as an antibody or antigen, or a single-stranded nucleic acid, which specifically connects with a target substance, is used as a probe and is fixed on a surface of a solid material, such as fine particles, beads or a glass plate, and an antigen-antibody reaction or nucleic acid hybridization is then performed with the target substance, Subsequently, an antigen-antibody compound or double-stranded nucleic acid is detected using a labeled substance supporting a labeling material, so that determination of the presence or absence of the target substance or quantitative determination thereof is performed, the target substance having a specific interaction with the probe. As the labeled substance, for example, there may be mentioned a labeled antigen, a labeled antibody, or a labeled nucleic acid. The labeling material has a high detection sensitivity, and for example, there may be mentioned an enzyme, a fluorescent material or a luminescent material.

As an extension of these techniques, for example, U.S. Pat. No. 5,445,934 has disclosed a so-called DNA (deoxyribonucleic acid) array in which a great number of DNA probes having mutually different base sequences are arranged on a substrate in array form.

In addition, Anal. Biochem., 270(1), pp. 103-111 (1999) has disclosed a process for preparing a protein array, like the DNA array, such that many types of proteins are arranged on a membrane filter. By using the DNA array, the protein array and the like, it has become possible to carry out a test including a considerably great number of items at the same time.

Furthermore, in various methods of sample analysis, in order to realize reduction of contamination by sample, promotion of reaction efficiency, reduction in apparatus size, simplification of operation and the like, there have also been proposed a disposable biochemical reaction cartridge in which a necessary reaction is performed therein. In addition, a system in which flow paths, reaction chambers, detectors, and the like are integrated by a micro-fabrication technique so that analysis, synthesis and/or the like is performed for a substance introduced therein is called μ-TAS (micro total analysis system), and research thereof has been aggressively performed. For example, PCT Japanese Translation Patent Publication No 11-509094 has disclosed a biochemical reaction cartridge, which is a μ-TAS including a DNA array, in which a plurality of chambers is disposed and a solution is moved by a differential pressure so as to allow reaction, such as extraction, amplification or hybridization of DNA in a sample, to proceed within the cartridge.

In addition, in U.S. Pat. No. 6,100,541, a μ-TAS in which an optical detection member is embedded adjacent to one of flow paths has been disclosed: In addition, although the following are not μ-TASs, a liquid measurement device has been disclosed in Japanese Patent Laid-Open No. 4-131763 which outputs an alarm in the case in which when a sample is recovered, the pressure does not reach a predetermined level after a predetermined time passes, and in Japanese Patent Laid-Open No. 11-304817, a dispenser device has been disclosed in which a suction amount and the number of suction and ejection during agitation are calculated based on a remaining amount of a sample which is determined from the liquid level thereof using a probe.

As a method for detecting the abnormality of movement of a liquid, a method for detecting a liquid in a flow path is generally performed; however, this method is not sufficient to detect leakage and clogging, and in addition, in the case of a μ-TAS, since the flow path thereof is very narrow, the structure becomes complicated and expensive. In addition, various methods for detecting the volume of liquid remaining in chambers or the like have also been proposed; however, in all the methods, the detection results obtained from individual chambers are independently used, and the normality of a process is not determined using a plurality of measurement results. Furthermore, there has been a method in which the abnormality is determined when the pressure is abnormal; however, since a fluid is not directly detected in this method, the detection result is not so much reliable.

SUMMARY OF THE INVENTION

The present invention provides a biochemical processing apparatus using a biochemical cartridge in which a liquid is moved, and in this biochemical processing apparatus, a normal flow of the liquid, causing no clogging nor leakage, can be reliably detected by a simple structure.

That is, a biochemical processing apparatus of the present invention comprises: a stage receiving a biochemical reaction cartridge which includes a plurality of chambers comprising at least one container chamber for containing a liquid for biochemical processing of a sample, at least one reaction chamber for performing biochemical processing of the sample, and at least one flow path communicating between the chambers; moving means for moving the liquid via the flow path; detecting means for detecting the presence or absence of the liquid or the amount thereof in at least one of the chambers; and determining means for determining a result of movement of the liquid from information on the liquid in said at least one of the chambers detected by the detecting means.

Although the biochemical processing apparatus of the present invention has a simple structure, the normal flow of liquid can be reliably detected, and it can be reliably determined whether the process is normal or abnormal. In addition, the abnormality of flow caused by various abnormal events such as clogging, leakage, and malfunction of a pump can be detected, and furthermore, since the abnormality of process can be detected at an early stage, the loss in time caused by reaction and inspection, which must be again performed, can be effectively reduced. In addition, when this biochemical processing apparatus is applied to a μ-TAS, an advantage is also obtained in which an abnormal position can be easily detected as compared with the case in which detection is performed in a flow path.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Figure 1:
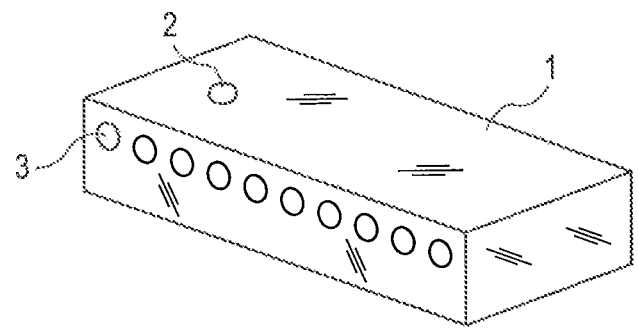
FIG. 1 is a perspective view of a biochemical reaction cartridge according to an embodiment of the present invention.

Preferred embodiments of the present invention will now be described in detail in accordance with the accompanying drawings.

In a biochemical reaction cartridge according to the present invention, having container chambers containing liquid for biochemically processing a sample, reaction chambers for performing biochemical processing of the sample, and flow paths communicating among the container chambers and the reaction chambers, in order to detect the liquid in each chamber with a sensor using light, a surface of the chamber facing the sensor is formed of a material transparent to light.

The chamber may be simply formed using a transparent material; however, in order to detect the amount of liquid in the chamber, when the bottom of the chamber is formed into a prismatic shape to project toward the liquid level, the amount of the liquid can be detected.

The liquid which is contained in the chamber may be stored beforehand in the chamber or may be supplied therein right before the processing is performed in a processing apparatus of the present invention.

The biochemical reaction cartridge described above is placed on a stage of a biochemical processing apparatus which has moving means for moving the liquid through the flow paths, detecting means for detecting the presence or absence of the liquid in the chambers and/or the amount thereof, and determining means for determining a result of the movement of the liquid from information on the liquid in the chambers obtained by the detecting means, so that biochemical reactions, such as extraction and amplification of DNA, are allowed to proceed while the liquid and the sample in the chambers are being moved.

The detecting means formed in the biochemical processing apparatus for detecting liquid information on liquid in the chambers can obtain liquid information on the presence or absence of the liquid or the amount thereof in both chambers from and to which the liquid is moved. The liquid information on each chamber is preferably detected at least before and after the liquid is moved.

In this embodiment, the above "after the liquid is moved" indicates "after a predetermined time" set beforehand at which the movement of the liquid from one chamber to another chamber is to be completed (chamber from which the liquid is moved is to be emptied), and after the predetermined time at which it is expected that said one chamber from which the liquid is moved is emptied, the presence or absence of the liquid in the chamber is detected, so that the abnormality may be determined when the liquid remains in said one chamber.

The abnormality may also be determined as described below. That is, the presence or absence of the liquid in said one chamber from which it is moved is detected at regular intervals, and when a time at which the liquid in the chamber is emptied is more than the predetermined time, the movement of the liquid may be determined as abnormal.

Furthermore, the biochemical processing apparatus preferably has another determining means for determining a liquid movement state from information on liquid in one chamber from which it is moved and information on the liquid in another chamber to which it is moved.

In a biochemical processing system, after the biochemical reaction cartridge described above is placed on a stage of a biochemical processing apparatus, for example, while liquid (such as a sample or cell lysis reagent) is being moved from one chamber to another chamber by applying the pressure to one side of a flow path using a gas (generally air) and by reducing the pressure at the other side of the flow path, biochemical reactions such as extraction and amplification of DNA are allowed to proceed so as to obtain information on the sample from a DNA array or the like in the biochemical reaction cartridge. Subsequently, by optical inspection or the like, the information on the sample is obtained.

In the following embodiments or examples, the biochemical processing apparatus and a detecting apparatus collecting information on a sample are described as if they are different from each other; however, of course, it is naturally understood that a detecting portion collecting information on a sample may be incorporated in the biochemical processing apparatus.

A biochemical processing system according to the present invention, comprises the biochemical reaction cartridge described above: a stage receiving the biochemical reaction cartridge; moving means for moving liquid via the flow paths; detecting means for detecting the presence or absence of the liquid and/or the amount thereof in the chambers of the biochemical reaction cartridge received on the stage, being located at positions corresponding to the chambers; and determining means for determining a result of movement of the liquid from information on the liquid in the chambers detected by the detecting means. The information on the liquid in the chambers preferably includes information on the liquid of chambers from and to which the liquid is moved, and the biochemical processing system preferably further comprises another determining means for determining a movement state of the liquid from the information on the liquid in the chambers from and to which the liquid is moved.

Control of the movement of liquid, according to the present invention, comprises: before liquid in one chamber is moved to another chamber via a flow path, a first detecting step of detecting first liquid information on the presence or absence of the liquid and/or the amount thereof in said one, or first, chamber and second liquid information on the presence or absence of the liquid or the amount thereof in said another, or second, chamber; and after the liquid in said one chamber is moved to said another chamber via the flow path, a second detecting step of detecting third liquid information on the presence or absence of the liquid or the amount thereof in said one chamber and fourth liquid information on the presence or absence of the liquid or the amount thereof in said another chamber.

In the above control of the movement of liquid, in the case in which the first, second, third, and fourth liquid information is information indicating the presence or absence of the liquid in the chambers, when the first information indicates the presence of the liquid in said one chamber, and the second information indicates the absence of the liquid in said another chamber, the liquid in said one chamber is moved to said another chamber. On the other hand, when the first information indicates the absence of the liquid in said one chamber, there is provided a step of outputting a signal indicating the abnormality.

Furthermore, after the liquid in said one chamber is moved to said another chamber, when the third information indicates the absence of the liquid in said one, chamber, and the fourth information indicates the presence of the liquid in said another chamber, it is determined that the movement of the liquid is normally completed, and when the third information indicates the presence of the liquid in said one chamber, there is provided a determining step of determining the movement of the liquid as abnormal.

From the liquid information obtained after the liquid in said one chamber is moved to said another chamber, when it is determined that the liquid is not normally moved, there are further provided a step of again moving the liquid in said one chamber to said another chamber, and a step of detecting a fifth liquid information indicating the presence or absence of the liquid in said one chamber. When the fifth liquid information indicates the absence of the liquid in said one chamber, the movement of the liquid is determined as normal, and when the fifth liquid information indicates the presence of the liquid in said one chamber, the movement of the liquid may be determined as abnormal, In the above control of the movement of liquid, in the case in which the first and the third liquid information is information indicating the presence or absence of the liquid in the chambers, and the second and the fourth liquid information is information indicating the amount of the liquid in the chambers, when the first information indicates the presence of the liquid in said one chamber, the liquid in said one chamber is moved to said another chamber, and when the first liquid information indicates the absence of the liquid in said one chamber, there may be provided a step of outputting a signal indicating the abnormality.

After the liquid in said one chamber is moved to said another chamber, when the third liquid information indicates the presence of the liquid in said one chamber, the movement of the liquid is determined as abnormal, and when the third liquid information indicates the absence of the liquid in said one chamber, it may be determined that the movement of the liquid is normally completed.

When the movement of the liquid is determined as abnormal, the processing is not finished in this step, and there are provided a step of again moving the liquid in said one chamber to said another chamber, and a step of detecting fifth liquid information on the presence or absence of the liquid in said one chamber. When the fifth liquid information indicates the absence of the liquid in said one chamber, there are provided a step of detecting sixth liquid information on the amount of the liquid on said another chamber, and a step of comparing the sixth liquid information with the fourth liquid information. When the amount of the liquid obtained from the sixth liquid information is larger than that obtained from the fourth liquid information, it is determined that the movement of the liquid is normally completed, and when the amount of the liquid obtained from the sixth liquid information is equal to or less than that obtained from the fourth liquid information, the movement of the liquid may be determined as abnormal. Of course, it is naturally understood that the above process may be performed a plurality of times.

When the first movement of the liquid is determined as normal, there is provided a step of comparing the fourth liquid information with the second liquid information, and when the amount of the liquid obtained from the fourth liquid information is larger than that obtained from the second liquid information, it is determined that the movement of the liquid is normally completed. On the other hand, when the amount of the liquid obtained from the fourth liquid information is equal to or less than that obtained from the second liquid information, the movement of the liquid may be determined as abnormal.

In addition, in the case in which the liquid in one chamber is moved to another chamber, and in which liquid information of said another chamber is detected at least once during the movement of the liquid, the liquid information is compared with liquid information obtained immediately therebefore, and when the amount of the liquid is increased, the movement of the liquid may be determined as normal. On the other hand, when the amount of the liquid is not increased, the movement of the liquid may be determined as abnormal. In this case, of course, while increase in amount of the liquid is being confirmed by continuously detecting the liquid information, the liquid may be moved. In the method described above, the movement of the liquid is regarded to be completed after a predetermined time from the movement of the liquid, and the liquid information is then detected; however, when the amount of the liquid is continuously measured, the completion of the, movement of the liquid may be determined when the increase in amount of the liquid is no longer detected.

Furthermore, when the amount of the liquid is not increased even after a predetermined time from the movement of the liquid, the movement of the liquid may also be determined as abnormal.

The above determination after a predetermined time from the movement of the liquid is made from the liquid information on the chamber to which the liquid is moved; however, the determination may also be made from the liquid information on the chamber from which the liquid is moved.

After the liquid is moved, when the presence or absence of the liquid in the chamber from which the liquid is moved is detected, and when the liquid is present therein, it may be determined that the movement of the liquid is not normally completed. However, instead of the case in which the movement of the liquid is determined from the liquid information on only one of the two chambers, when the liquid information on a chamber from which the liquid is moved and that of a chamber to which the liquid is moved are detected before and after the movement of the liquid as is the case of the present invention, and when processing is performed while the state of the movement of liquid is determined, the processing can be more reliably carried out.

EXAMPLE

An example of the present invention will be described in detail with reference to the drawings, FIG. 1 is a perspective view showing the appearance of a biochemical reaction cartridge 1 of this example. In the upper wall of the cartridge 1, a sample inlet 2 is provided through which a sample such as blood is injected using a syringe and is sealed with a rubber cap. In addition, in one side wall of the cartridge 1, a plurality of nozzle inlets 3 is formed in which nozzles are inserted for applying or reducing the pressure so as to move liquid present inside, and rubber caps are fixed in the individual nozzle inlets 3. In the other side wall facing to the above side wall, the same structure is formed as described above.

Figure 2:
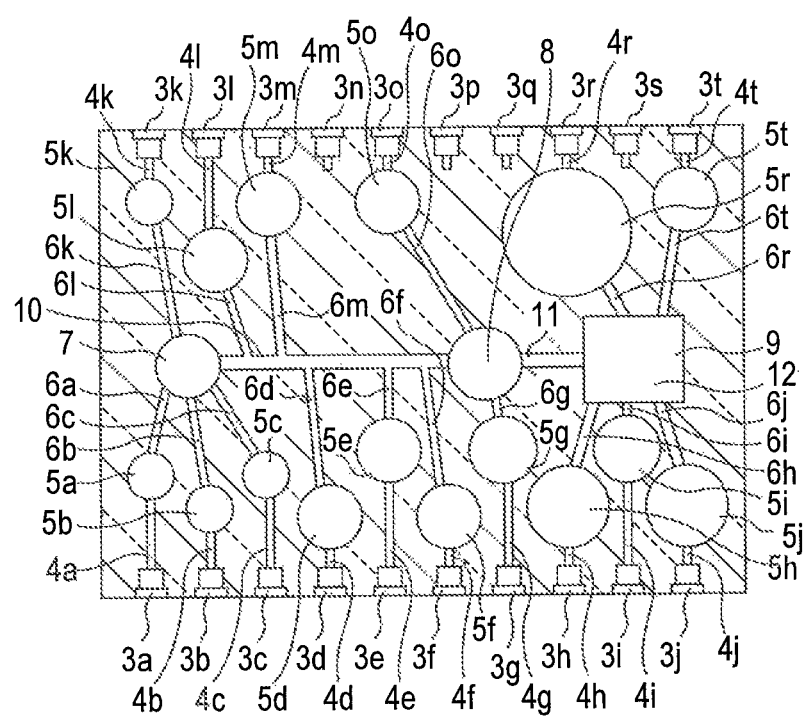
FIG. 2 is a plan cross-sectional view of a biochemical reaction cartridge according to the present invention.

A main body of the biochemical reaction cartridge 1 is formed of a transparent material, polymethylmethacrylate (PMMA) in this example. When a reaction product in the cartridge 1 is required to be measured using an optical technique, or when the presence or absence of liquid or the amount thereof is optically measured, a portion through which light is allowed to pass for the above measurement may only be formed of a transparent or semitransparent material, and the other portion may be formed of an opaque material, FIG. 2 is a plan cross-sectional yield of the biochemical reaction cartridge 1, 10 nozzle inlets $3a$ to $3j$ are formed in one side wall, and in the other side wall facing thereto, 10 nozzle inlets $3k$ to $3t$ are formed.

The nozzle inlets $3a$ to $3t$ are formed to communicate with respective chambers 5 via air flow paths $4a$ to $4t$ through which air is allowed to flow, and in the chambers 5, liquid is stored, reaction occurs, or liquid is mixed. However, in a process of this example, since being not used, the nozzle inlets $3n$, $3p$, $3q$, and $3s$ do not communicate with the chambers 5 and are formed as backup inlets. That is, the nozzle inlets $3a$ to $3j$ communicate with the respective chambers $5a$ to $5j$ via the flow paths $4a$ to $4$, and the nozzle inlets $3k$, $31$, $3m$, $3o$, $3r$, and $3t$ located at the opposite side communicate with the respective chambers $5k$, $51$, $5m$, $5o$, $5r$, and $5t$ via the flow paths $4k$, $4l$, $4m$, $4o$, $4r$, and $4t$. The sample inlet 2 communicates with a chamber 7, the chambers $5a$, $5b$, $5c$, and $5k$ communicate with the chamber 7, the chambers $5g$ and $5o$ communicate with a chamber 8, and the chambers $5h$, $5i$, $5j$, $5r$ and $5t$ communicate with a chamber 9. Furthermore, the chamber 7 communicates with the chamber 8 via a flow path 10, and the chamber 8 communicates with the chamber 9 via a flow path 11. The chambers $5d$, $5e$, $5f$, $5l$, and $5m$ communicate with the flow path 10 via flow paths $6d$, $6e$, $6f$, $6l$, and $6m$, respectively.

In addition, at the bottom of the chamber 9, a square hole is formed, and a DNA microarray 12 is adhered to this square hole so that probes thereof face upward, the DNA microarray 12 containing several tens to several hundred thousands of different types of DNA probes on a solid surface of a glass plate or the like having an area of approximately one square inch.

When a hybridization reaction is performed with sample DNA using this DNA microarray 12, a great number of genes can be inspected at the same time. In addition, the DNA probes described above are regularly disposed in a matrix, and hence addresses (position at the number of row and at the number of column) of the individual DNA probes can be easily obtained as information. As genes to be inspected, in addition to infective viruses, bacteria, and disease-associated genes, genetic polymorphism of an individual may also be mentioned by way of example.

In the chambers $5a$ and $5b$, a first cell lysis reagent containing ethylenediaminetetraacetic acid (EDTA) digesting a cell membrane and a second cell lysis reagent containing a protein modifier such as a surfactant are stored, respectively. In the chamber $5c$, magnetic particles coated with silica for adsorbing DNA are stored, and in the chambers $5l$ and $5m$, a first and a second extraction wash buffer for purifying DNA in extraction thereof are stored, respectively.

In the chamber $5d$, an elution buffer, comprising a buffer of a low-concentration salt, for eluting DNA from the magnetic particles is stored, and a mixture liquid (hereinafter referred to as "PCR mixture") for a polymerase chain reaction (PCR), comprising a primer, polymerase, deoxyribonucleotide triphosphate (dNTP) liquid, a buffer, Cy-3dUTP containing a fluorescent agent and the like, is stored in the chamber $5g$. In the chambers $5h$ and $5j$, a first and a second wash buffer containing a surfactant are stored, respectively, which are used for washing fluorescence-labeled sample DNA which is not subjected to hybridization, and a fluorescence labeling material, In the chamber $5i$, an alcohol for drying the inside of the chamber 9 including the DNA microarray 12 is stored.

In the chamber $5e$, the rest of blood other than DNA is stored; in the chamber $5f$, waste liquid of the first and the second extraction wash buffer contained in the chambers $5l$ and $5m$, respectively, is stored; and in the chamber $5r$, waste liquid of the first and the second wash buffer is stored.

In addition, the chambers $5k$, $5o$, and $5t$ are blank chambers provided for preventing liquid from flowing into the nozzle inlets, and even when the liquid is splashed to form droplets, they are not allowed to enter the nozzle inlets.

When a liquid sample such as blood is injected into this biochemical reaction cartridge 1 and is then set in a processing apparatus which will be described later, extraction and amplification of DNA or the like are carried out inside the cartridge 1. Subsequently, hybridization between amplified sample DNA and the DNA probes on the DNA microarray provided in the cartridge 1 is carried out, and fluorescent labeled sample DNA, which is not subjected to hybridization, and the fluorescent labeling material are washed out.

Figure 3:
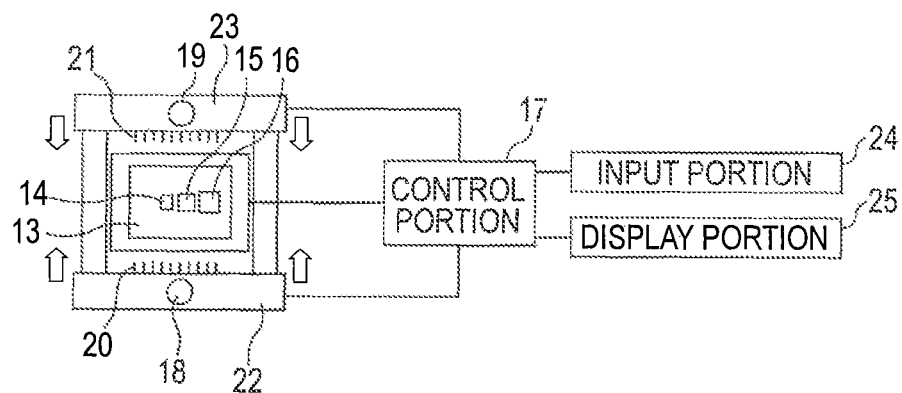
FIG. 3 is a block diagram of a processing apparatus controlling movement of liquid and various reactions in a biochemical reaction cartridge, according to the present invention.

FIG. 3 is a schematic view of a processing apparatus controlling the movement of liquid and various reactions in the biochemical reaction cartridge 1. A table 13 is the position on which the cartridge 1 is disposed, and on this table 13, the following constituent elements are disposed and are connected to a control portion 17 controlling the whole processing apparatus. The constituent elements are an electromagnet 14 to be operated when DNA or the like is extracted from a sample in the cartridge 1; a Peltier element 15 controlling the temperature when DNA extracted from the sample is amplified by a method such as a polymerase chain reaction (PCR); a Peltier element 16 controlling the temperature when hybridization between amplified sample DNA and the DNA probes on the DNA microarray in the cartridge 1 is performed and when sample DNA which is not subjected to hybridization is washed out; and liquid sensor units $26a$, $26d$, $26f$, $26h$, $26l$, $26m$, $29k$, and $29r$ shown in FIG. 4.

On two sides of the table 13, there are provided electric syringe pumps 18 and 19, and pump blocks 22 and 23 having 10 pump nozzles 20 and 10 pump nozzles 21, respectively, the pump blocks 22 and 23 functioning as an inlet and an outlet through which air is supplied or sucked by the pumps 18 and 19. Between the electric syringe pump 18 and the pump nozzles 20 and between the electric syringe pump 19 and the pump nozzles 21, a plurality of electric switching valves (not shown) is disposed and is also connected to the control portion 17 together with the pumps 18 and 19. In addition, an input portion 24 to which an operator inputs data and a display portion 25 on which information is displayed are connected to the control portion 17, The control portion 17 performs various Controls such that one of 10 pump nozzles 20 and one of 10 pump nozzles 21 are selectively opened to the electric syringe pumps 18 and 19, respectively, or such that all the pump nozzles are closed.

In this example, when blood which is a sample is injected into the cartridge 1 through the rubber cap fitted in the sample inlet 2 by an operator using a syringe, the blood is allowed to flow into the chamber 7. Subsequently, when the operator places the biochemical reaction cartridge 1 on the table 13 and operates a lever (not shown) to move the pump blocks 22 and 23 in the directions shown in FIG. 3, the pump nozzles 20 and 21 penetrate the rubber caps fitted in the nozzle inlets 3 provided at both sides of the cartridge 1 so as to be inserted thereinto.

In addition, since the nozzle inlets 3a to 3t are concentratedly formed at two sides of the biochemical reaction cartridge 1 facing each other, the shapes and dispositions of the electric syringe pumps 18 and 19, the pump blocks 22 and 23 incorporating the electric switching valves and the pump nozzles, and the like can be simplified. Furthermore, by simple operation of simultaneously holding the cartridge 1 from the two sides thereof by the pump blocks 22 and 23 while necessary chambers 5 and flow paths are secured, the pump nozzles 20 and 21 can be inserted into the cartridge 1, and as a result, the structures of the pump blocks 22 and 23 can also be simplified. In addition, since the nozzle inlets 3a to 3t are disposed at the same height, that is, since they are linearly disposed, the flow paths 4a to 4t connected to the respective nozzle inlets 3a to 3t are all located at the same height, and as a result, the flow paths 4a to 4t can be easily formed.

Figure 4:
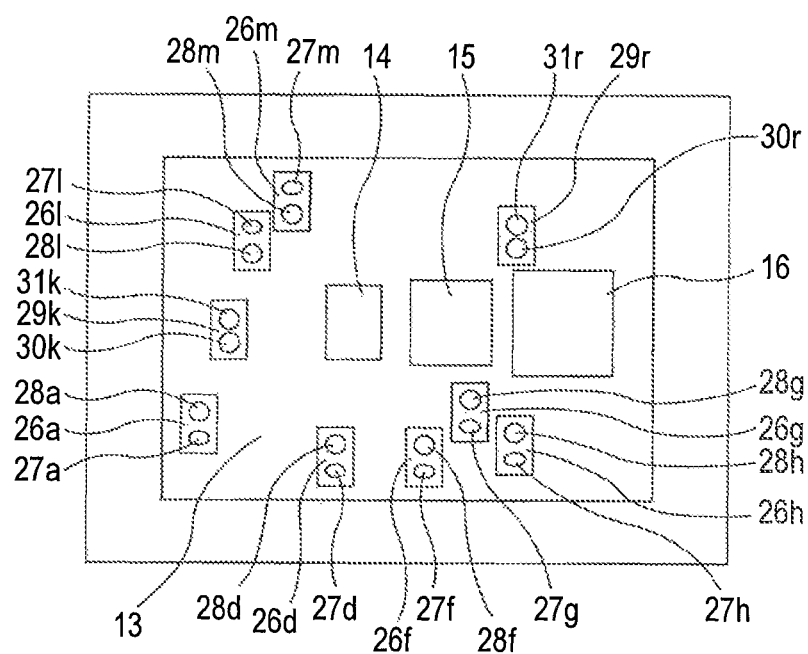
FIG. 4 is a detailed view of a table shown in FIG. 3, according to the present invention.

In addition, in the processing apparatus shown in FIG. 3, when the length of the pump blocks 22 and 23 are increased by n times the length thereof, and n biochemical reaction cartridges 1 are disposed linearly, necessary processing for the n biochemical reaction cartridges 1 can be simultaneously performed, and hence, although the structure is significantly simplified, biochemical reactions can be carried out in many cartridges, FIG. 4 is a view showing the table 13 in detail, and the liquid sensor units 26a to 26m, 29k, and 29r described above are shown. The above liquid sensor units are composed of light sources, such as LEDs, 27a, 27d, 27f, 27g, 27h, 27l, 27m, 30k, and 30r, and light-receiving elements, such as photodetectors, 28a, 28d, 28f, 28g, 28h, 28l, 28m, 31k, and 31r, respectively.

Figure 5:
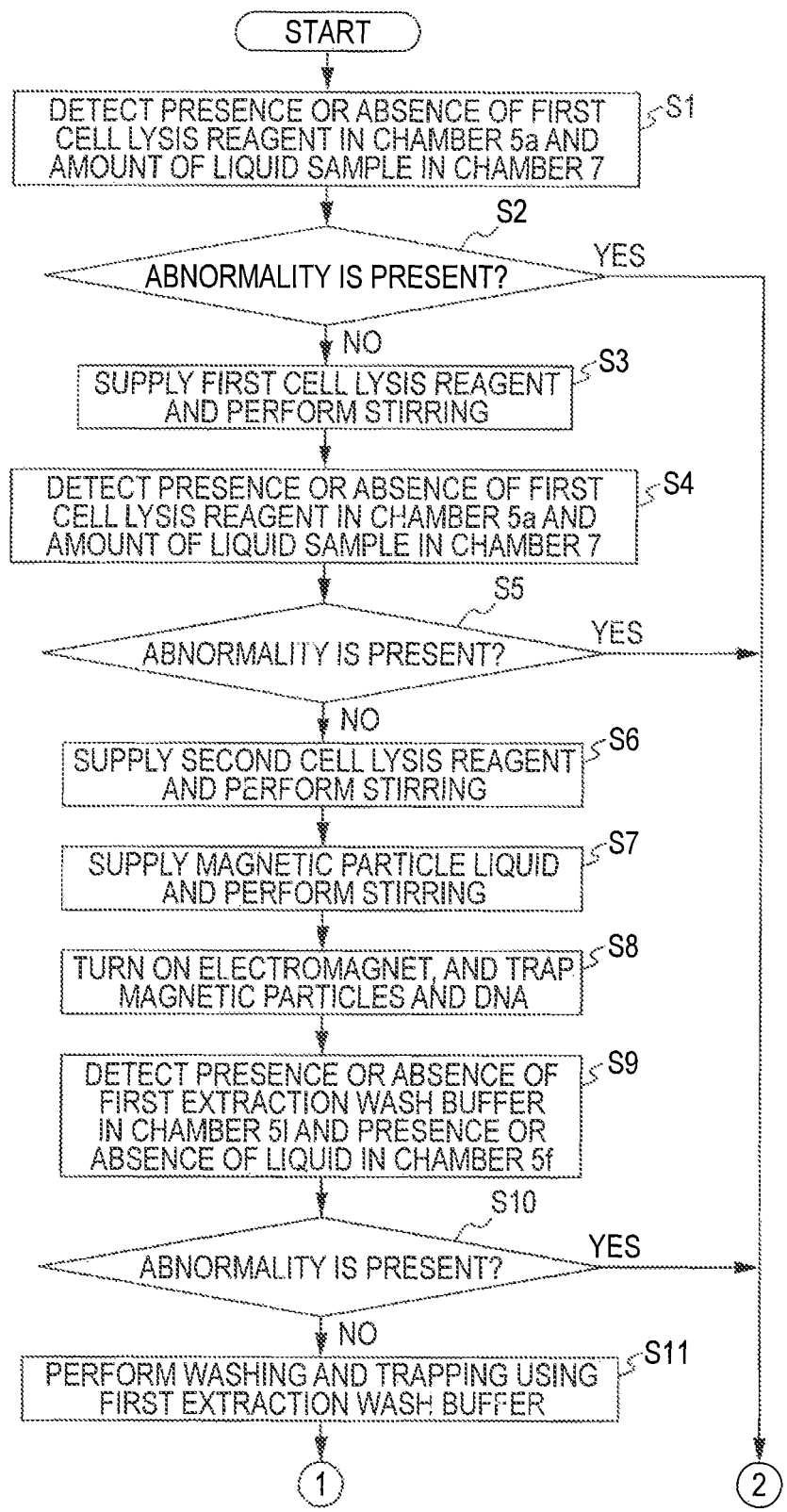
FIG. 5 is a flowchart of a processing procedure according to the present invention.
Figure 6:
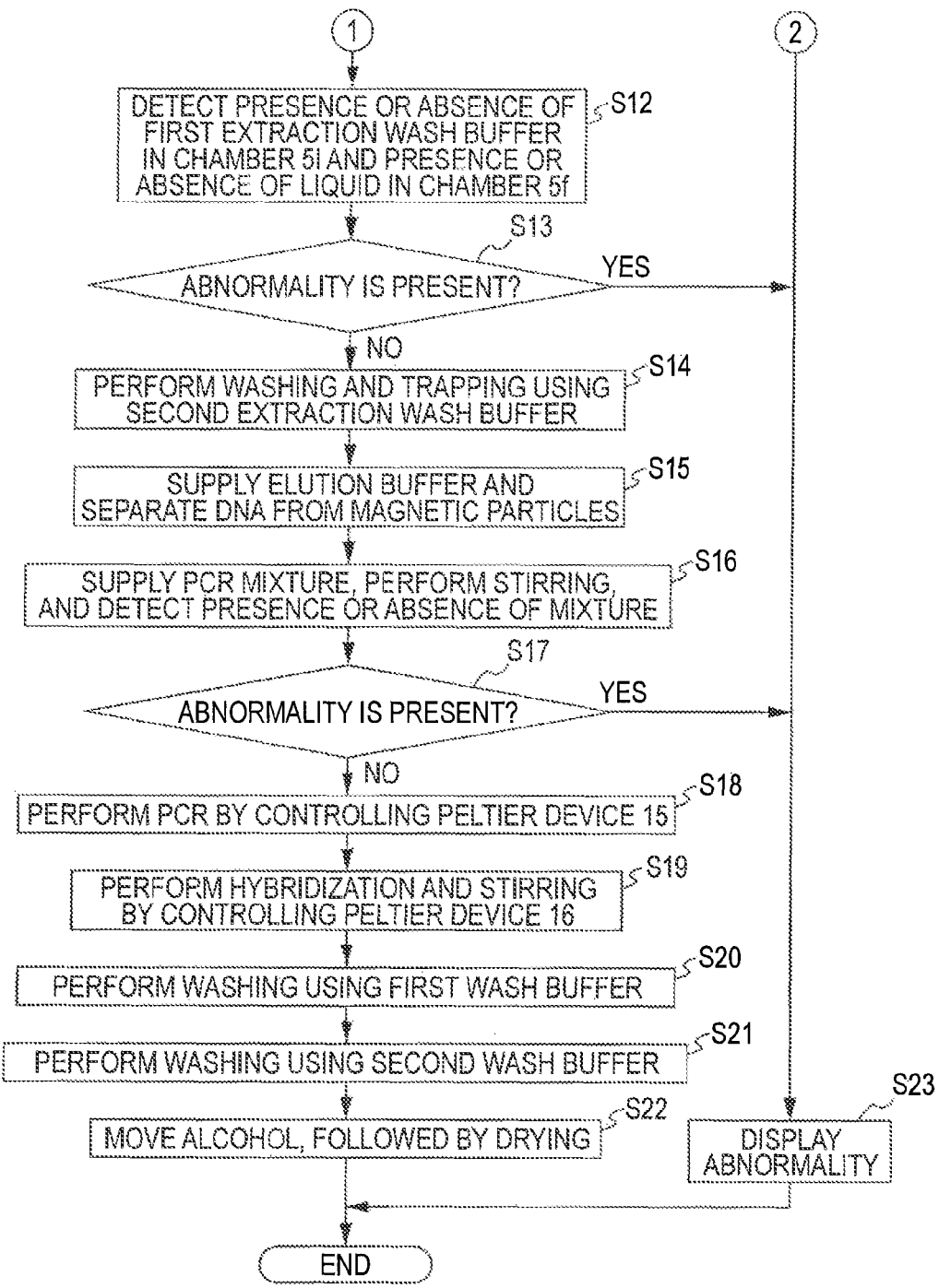
FIG. 6 is a flowchart of a processing procedure according to the present invention.

Next, flowcharts in FIGS. 5 and 6 showing a process of the present invention and the structure of the biochemical reaction cartridge 1 for implementing the process will be described with reference to drawings.

At "Start" in the flowchart showing the process, an operator inputs a command of starting the process in the input portion 24, and by the command thus inputted therein, the processing apparatus starts the process.
(Step S1)

In Step S1, the processing apparatus detects the presence or absence of the first cell lysis reagent in the chamber 5a and the amount of a liquid sample in the chamber The control portion 17 detects the presence or absence of the first cell lysis reagent in the chamber 5a using the liquid sensor unit 26a and the amount of the liquid sample in the chamber 7 using the liquid sensor unit 29k.

Figure 7:
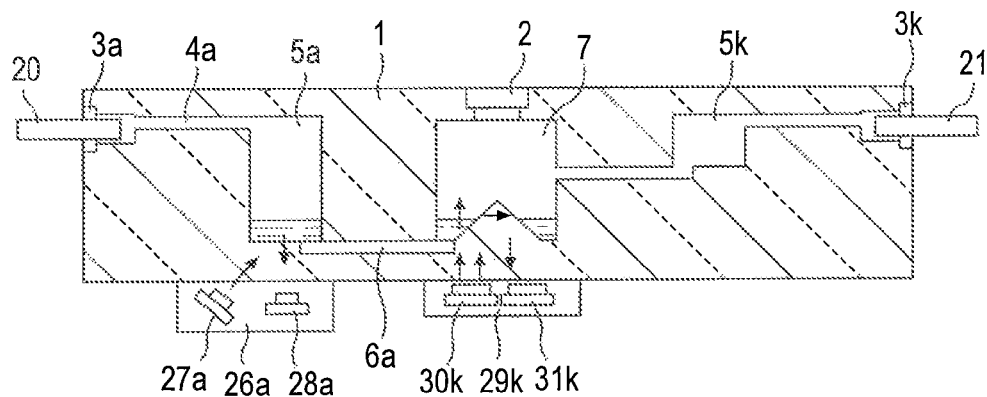
FIG. 7 is a vertical cross-sectional view showing some chambers and liquid sensor units, according to the present invention.

FIG. 7 is a vertical cross-sectional view of the cartridge 1 taken along a line passing through the chambers 5a, 7, and 5k shown in FIG. 2. In this figure, the state is shown in which the first cell lysis reagent and a blood sample are contained in the chamber 5a and the chamber 7, respectively. At the lower side of the chamber 5a, the liquid sensor unit 26a is provided, the bottom of the chamber 5a is obliquely irradiated by light emitted from the LED 27a used as a light source, scattered light generated from the liquid thereby is partly incident on the photodetector 28a and is then converted into an electrical signal, and this electrical signal is transmitted to the control portion 17.

In order to prevent light of the LED 27a reflected on the interface between the cartridge 1 and the first cell lysis reagent from directly entering the photodetector 28a, the LED 27a is obliquely disposed. For example, in consideration of the directional characteristics of the output of the LED 27a and the directional characteristics of the sensitivity of the photodetector 28a, this angle may be determined so that the direct reflection light of the LED 27a is below the sensitivity of the photodetector 28a. When the liquid is not present in the chamber 5a, since scattered light is not generated from the liquid, no electrical signal is generated from the photodetector 28a. As described above, the presence or absence of the liquid can be determined. In addition, since the amount of the liquid and the amount of scattered light correspond to each other, when the correspondence is investigated beforehand for various types of liquid, the amount of the liquid can be detected by using a light-receiving element having superior sensitivity.

In addition, at the lower side of the chamber 7, the liquid sensor unit 29k is provided, and the material forming the cartridge 1 at the bottom surface of the chamber 7 is projected in the form of a prism. The bottom of the chamber 7 is irradiated with light emitted from the LED 30k used as a light source, and when liquid is present in the chamber 7, since the refractive index (1.49) of polymethylmethacrylate used as a material for the cartridge 1 and the refractive index (although varying depending on components, approximately 1.34) of blood is close to each other, most irradiation light passes through upwardly. When the liquid is not present, since the refractive index of polymethylmethacrylate and the refractive index (1.0) of air are considerably different from each other, most irradiation light is reflected on the interface therebetween, is also reflected on the other interface, and is then received by the photodetector 31k, so that a signal is then transmitted to the control portion 17. As described above, since the height of the liquid level and the amount of reflection light correspond to each other, the amount of liquid can be detected. Other typical transparent synthetic resins besides polymethylmethacrylate, that is, polycarbonate, polyethylene, polypropylene, polyvinyl chloride, and silicone resin and the like, have a refractive index in the range of 1.43 to 1.59, and a magnetic particle liquid, elution buffer, PCR mixture, wash buffer, alcohol used in this example have a refractive index in the range of approximately 1.33 to 1.5, so that these refractive indexes are close to each other and are different from that of air. Hence, a method for using reflection light can be employed. Of course, combination of materials in which the difference in refractive index smaller is more preferably used. In addition, a method using scattered light can be advantageously used for liquid containing a large amount of particles, such as the magnetic particle liquid or blood, since the amount of scattered light generated therefrom is large.

The methods described above are each a method for detecting the presence or absence of the liquid or the amount thereof in an optical manner from the outside of the biochemical reaction cartridge, and hence a specific member provided inside the biochemical reaction cartridge s not required at all.
(Step S2)

Whether the abnormality is present, such that the liquid is not present, or the amount thereof is not sufficient, is determined in Step S2 from the detection result in Step S1, and when the abnormality is not present, Step S3 is then performed. On the other hand, when the abnormality is present, information indicating the abnormality is displayed on the display portion 25 in Step S23, and the process is finished.
(Step S3)

In Step S3, the first cell lysis reagent is supplied and stirred. Only the nozzle inlets 3a and 3k are opened, air is supplied from the electric syringe pump 18, and air is sucked by the pump 19, so that the first cell lysis reagent in the chamber 5a is supplied to the chamber 7 containing the blood. In this step, although depending on the viscosity of the cell lysis reagent and the flow resistance of the flow path, when the suction of air by the pump 19 is controlled to start 10 to 200 milliseconds after the supply of air from the pump 18, the front end of flowing liquid is not splashed, and hence the liquid is allowed to flow smoothly.

As described above, when the timing of the suction of air is shifted from that of the supply of air so as to control the application and reduction of pressure, the liquid is allowed to flow smoothly. In addition to that, when the suction of air by the electric syringe pump 19 is precisely controlled such that the amount of air sucked by the electric syringe pump 19 is linearly increased from the start of the supply of air by the pump 18, the liquid is allowed to flow more smoothly. The movement of liquid described below is the same as described above.

Since the control of supply of air can be easily realized by using the electric syringe pumps 18 and 19, while only the nozzle inlets 3a and 3o are opened, the supply and suction of air are alternately repeated using the pumps 18 and 19 so that the liquid in the chamber 7 is reciprocated back and forth in the flow path 10, and hence the liquid is stirred. Alternatively, the liquid may be stirred by generating bubbles while air is continuously supplied from the pump 19.
(Step S4)

Next, in Step S4, the presence or absence of the first cell lysis reagent in the chamber 5a and the amount of the sample in the chamber 7 are detected. After the time in which all the first cell lysis reagent is to be moved from the chamber 5a to the chamber 7, in the same manner as that in Step S1, the presence or absence of the first cell lysis reagent in the chamber 5a is detected using the liquid sensor unit 26a, and the amount of the liquid in the chamber 7 is also detected using the liquid sensor unit 29k.
(Step S5)

Figure 8:
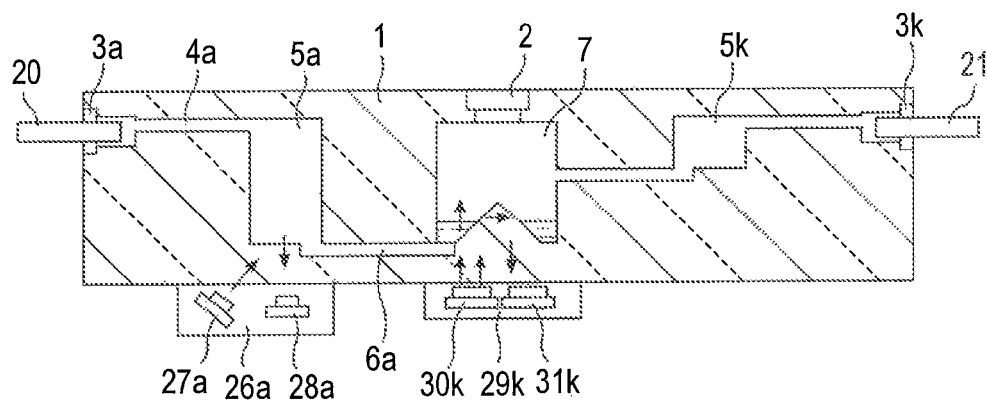
FIG. 8 is a vertical cross-sectional view showing some chambers and liquid sensor units, according to the present invention.

Since the first cell lysis reagent in the chamber 5a is supplied to the chamber 7 and stirred in Step S3, it is determined whether the chamber 5a is empty and a predetermined amount of the liquid is present in the chamber 7 as shown in FIG. 8.

Figure 9:
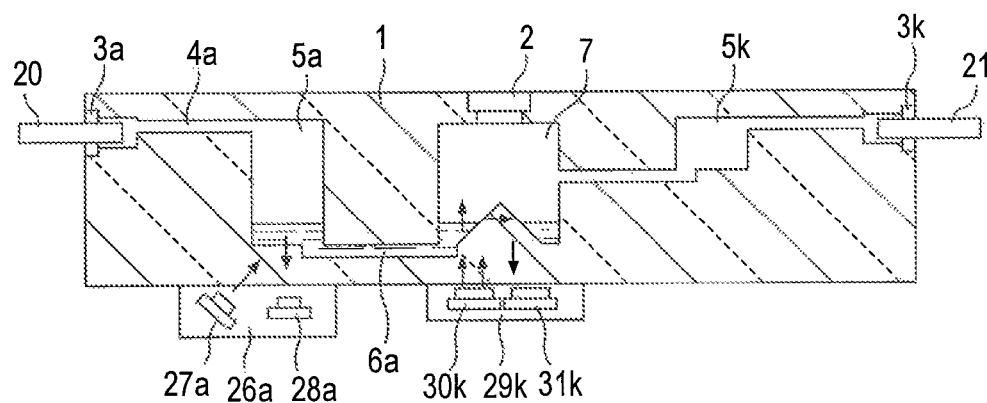
FIG. 9 is a vertical cross-sectional view showing some chambers and liquid sensor units, according to the present invention.

For example, in the casein which the movement of the liquid is not ideally carried out since the flow path is clogged, or some abnormal event occurs in the electric syringe pumps, electrical switching valves, flow paths, or the like, as shown in FIG. 9, the amount of light received by the photodetector 28a is increased since the liquid remains in the chamber 5a, and the amount of light received by the photodetector 31k is increased since, the amount of the liquid in the chamber 7 is insufficient. In the case described above, when the above state is still maintained even after a predetermined time passes, it is determined that the abnormality occurs, the process is allowed to proceed to Step S23, information indicating the abnormality is displayed on the display portion 25, and the process is finished.

As described above, when the presence or absence of the first cell lysis reagent in the chamber 5a and the amount of the liquid in the chamber 7 are detected before and after (plurality of times) the movement of the first cell lysis reagent, it can be determined whether the cell lysis reagent is appropriately moved.

When only the amount of the liquid in the chamber 7 is detected, it is not determined which type of liquid is supplied, and precise detection cannot be performed. In addition, in this example, detection is only performed before and after (plurality of times) the movement of the cell lysis reagent; however, detection may be more frequently or continuously performed. Furthermore, in Step S5, in the case in which the chamber 5a is not empty, the abnormality is determined when the chamber 5a is still not empty after a predetermined time passes. However, the abnormality may also be determined as follows That is, after the first cell lysis reagent is being supplied until the chamber 5a is emptied, the time required therefor is compared with a predetermined time required for emptying the chamber, and when the time is longer than the predetermined time, the movement of the liquid is determined as abnormal,
(Step S6)

Next, the second cell lysis reagent in the chamber 5b is supplied to the chamber 7 and is stirred. Only the nozzle inlets 3b and 3k are opened, and the second cell lysis reagent in the chamber 5b is supplied to the chamber 7 and is stirred.
(Step S7)

Subsequently, in Step S7, the magnetic particle liquid in the chamber 5c is supplied to the chamber 7 in the same manner as described above. While only the nozzle inlets 3c and 3k are opened, the magnetic particle liquid in the chamber 5c is supplied to the chamber 7.

In Steps S6 and S7, stirring is performed in the same manner as that in Step S3. In Step S7, DNA obtained by dissolving cells in Steps S3 and S6 adheres to the magnetic particles.
(Step S8)

Step S8, the electromagnet is turned on, and DNA is trapped on the magnetic particles. The electromagnet 14 is turned on, only the nozzle inlets 3e and 3k are opened, air is supplied from the electric syringe pump 19, and air is sucked by the pump 18, so that the liquid in. the chamber 7 is moved to the chamber 5e. During this movement, the magnetic particles and DNA are trapped in the flow path 10 located above the electromagnet 14. The supply and suction of air by the pumps 18 and 19 are alternately repeated to reciprocate the liquid back and forth between the chamber 7 and the chamber 5e twice, so that the trapping efficiency of DNA is improved. In addition, when the number of reciprocating movements is increased, the trapping efficiency can be further improved; however, the time required for processing is increased.

As described above, while being flowing, DNA is trapped using the magnetic particles in a small flow path having a width of approximately 1 to 2 mm and a height of approximately 0.2 to 1 mm, and hence the trapping efficiency can be significantly increased. In addition, when a trapping target substance is RNA or protein, a similar trapping efficiency to that described above can also be obtained.
(Step S9)

Next, in Step S9, the control portion 17 detects the presence or absence of the first extraction wash buffer in the chamber 5l using the liquid sensor unit 26l and the presence or absence of the liquid in the chamber 5f using the liquid sensor unit 26f.

Figure 10:
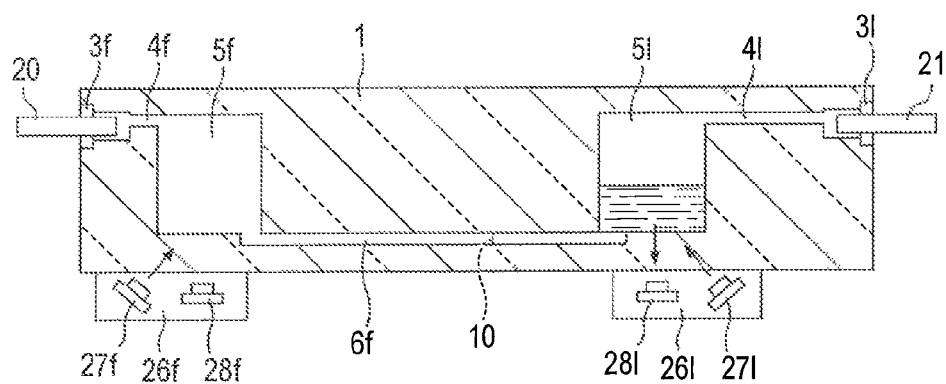
FIG. 10 is a vertical cross-sectional view showing some other chambers and liquid sensor units, according to the present invention.

FIG. 10 is a vertical cross-sectional view of the cartridge 1 taken along a line passing through the chambers 5l and 5f, showing the state in which the first extraction wash buffer is contained in the chamber 5l. As is the liquid sensor unit 26a, the liquid sensor unit 26l is provided at the lower side of the chamber 5*l*, the bottom of the chamber 5*l* is obliquely irradiated by light emitted from the LED 27*l* used as a light source, scattered light is thereby generated from the liquid and is partly received by the photodetector 28*l*, and a signal is transmitted to the control portion 17. The liquid sensor unit 26*f* equivalent to the liquid sensor unit 26*a* is also provided at the lower side of the chamber 5*f*, the bottom of the chamber 5*f* is obliquely irradiated by light emitted from the LED 27*f* used as a light source, scattered light is thereby generated from the liquid and is partly received by the photodetector 28*f*, and a signal is transmitted to the control portion 17.

(Step S10)

In Step S10, from the detection result in Step S9, it is determined whether the first extraction wash buffer is present in the chamber 5*l* and whether the chamber 5*f* is empty. When the abnormality is detected, the process is allowed to proceed to Step S23, and information indicating the abnormality is displayed on the display portion 25, so that the process is finished. When the abnormality is not detected, the process is allowed to proceed to Step S11.

(Step S11)

in Step S11, washing and trapping is performed using the first extraction wash buffer. The electromagnet 14 is turned off, only the nozzle inlets 3*f* and 3*l* are opened, air is supplied from the electric syringe pump 19, and air is sucked by the pump 18, so that the first extraction wash buffer in the chamber 5*l* is moved to the chamber 5*f*. In this movement, the magnetic particles and DNA trapped in Step S4 are also moved together with the extraction wash buffer, so that washing is performed.

(Step S12)

Next, in Step S12, the presence or absence of the first extraction wash buffer in the chamber 5*l* and the presence or absence of the liquid in the chamber 5*f* are detected.

After the time in which all the first extraction wash buffer is moved from the chamber 5*l* to the chamber 5*f*, in the same manner as that in Step S9, the presence or absence of the first extraction wash buffer in the chamber 5*l* and the presence or absence of the liquid in the chamber 5*f* are detected by using the liquid sensor units 26*l* and 26*f*, respectively.

(Step S13)

Next, in Step S13, it is determined whether the chamber 5*l* is empty and whether the first extraction wash buffer is present in the chamber 5*f*, and when the chamber 5*l* is not empty, and the first extraction wash buffer is not present in the chamber 5*f*, after a predetermined time passes, the states of the chambers are again detected. When the states are Still not changed from that described above, it is determined that the abnormality occurs, the process is allowed to proceed to Step S23, information indicating the abnormality is displayed on the display portion 25, and the process is finished.

Figure 11:
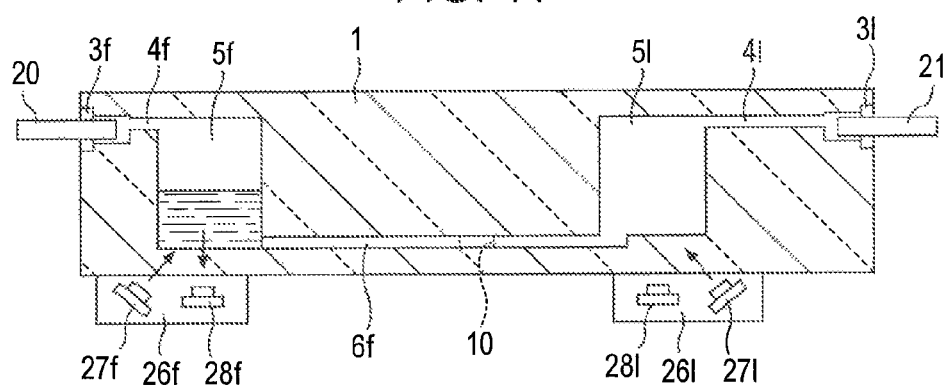
FIG. 11 is a vertical cross-sectional view showing some other chambers and liquid sensor units, according to the present invention.

As shown in FIG. 11, when the chamber 5*l* is empty, and the first extraction wash buffer is present in the chamber 5*f*, after the liquid is reciprocated back and forth twice as is the case in Step S8, the electromagnet 14 is turned on, and the liquid is reciprocated back and forth twice in the same manner as described above. Accordingly, the magnetic particles and DNA are trapped in the flow path 10 located above the electromagnet 14, and the liquid is returned to the chamber 5*l*, In this case, detection and determination in Steps S9, S10, S12, and S13 may be repeatedly performed.

(Step S14)

Next, washing and trapping by the second extraction wash buffer is performed. By using the nozzle inlets 3*f* and 3*m*, washing is further performed by the second extraction wash buffer in the chamber 5*m* in the same manner as that in Step S11, In this step, the presence or absence of the second extraction wash buffer in the chamber 5*m* and the presence or absence of the liquid in the chamber 5*f* are detected using the liquid sensor units 26*m* and 26*f*, respectively; however, since being the same as those in Steps S9 to S13, the procedures are not shown in the flowchart, and description thereof is omitted.

(Step S15)

Next, the elution buffer is allowed to flow, so that the magnetic particles and DNA are separated from each other.

While the electromagnet 14 is being placed in an ON-state, only the nozzle inlets 3*d* and 3*o* are opened, air is supplied from the electric syringe pump 18, and air is sucked by the pump 19, so that the elution buffer in the chamber 5*d* is moved to the chamber 8.

In this step, the magnetic particles and DNA are separated from each other by the effect of the elution buffer, only DNA is moved to the chamber 8 together with the elution buffer, and the magnetic particles remain in the flow path 10 As described above, the extraction and purification of DNA are performed.

(Step S16)

Next, in Step S16, the PCR mixture is supplied and stirred, and the presence or absence of the liquid is detected.

Only the nozzle inlets 3*g* and 3*o* are opened, air is supplied by the electric syringe pump 18, and air is sucked by the pump 19, so that the PCR mixture in the chamber 5*g* is supplied to the chamber 8. In addition, only the nozzle inlets 3*g* and 3*t* are opened, and the supply and suction of air are alternately repeated by the pumps 18 and 19 so as to reciprocate the liquid back and forth between the flow path 11 and the chamber 8, thereby performing stirring. In this step, the control portion 17 detects the presence or absence of the liquid in the chamber 5*g* using the liquid sensor unit 26*g*.

(Step S17)

Based on the detection result of the presence or absence of the liquid in the chamber 5*g* in Step S16, it is determined in Step S17 whether the abnormality is present, and when the liquid is not present in the chamber 5*g*, the process is allowed to proceed to Step S18. When the liquid is present in the chamber 5*g*, it is determined that the abnormality is present, the process is allowed to proceed to Step S23, information indicating the abnormality is displayed on the display portion 25, and the process is finished.

(Step S18)

In addition, in Step S18, after the liquid in the chamber 8 is maintained at 96° C. for 10 minutes by controlling the Peltier element 15, a thermal cycle including conditions at 96° C. for 10 seconds, 55° C. for 10 seconds, and 72° C. for 1 minute is repeated 30 times, so that the eluted DNA is amplified by PCR.

(Step S19)

In Step S19, hybridization and stirring are performed by controlling the Peltier element 16.

Only the nozzle inlets 3*g* and 3*t* are opened, air is supplied from the electric syringe pump 18, and air is sucked by the pump 19, so that the liquid in the chamber 8 is moved to the chamber 9. In addition, by controlling the Peltier element 16, the liquid in the chamber 9 is maintained at 45° C. for 2 hours in order to perform hybridization. In this step, while the supply and suction of air are alternately repeated by the pumps 18 and 19 so as to reciprocate the liquid back and forth between the chamber 9 and the flow path 6*t* for stirring, the hybridization is promoted.

(Step S20)

Next, in Step S20, washing is performed using the first wash buffer.

While the temperature is being maintained at 45° C. as is the case described above, in this step, only the nozzle inlets 3*h* and 3*r* are opened, air is supplied from the electric syringe pump 18, and air is sucked by the pump 19, so that the first wash buffer in the chamber 5*h* is supplied to the chamber 5*r* via the chamber 9 while the liquid in the chamber 9 is moved to the chamber 5*r*. In this step, the presence or absence of the first wash buffer in the chamber 5*h* and the amount of the liquid in the chamber 5*r* are detected using the liquid sensor unit 26*h* and the liquid sensor unit 29*r*, respectively; however, since being the same as those in Steps S1 to S5, the procedures thereof are not shown in the flowchart, and description thereof is omitted. The supply and suction of air by the pumps 18 and 19 are alternately repeated so as to reciprocate the liquid back and forth between the chambers 5*h*, 9, and 5*r* twice, and finally the liquid is returned to the chamber 5*h*. As described above, the fluorescence-labeled sample DNA which are not subjected to hybridization and the fluorescence labeling material are washed out.

(Step S21)

Next, in Step S21, washing using the second wash buffer is performed.

While the temperature is maintained at 45° C. as in Step S20, by using the nozzle inlets 3*j* and 3*r*, washing is performed using the second wash buffer in the chamber 5*j* by the same procedure as that in Step S20, and the wash buffer is finally returned to the chamber 5*j*.

(Step S22)

In Step 22, only the nozzle inlets 3*i* and 3*r* are opened, air is supplied by the electric syringe pump 18, and air is sucked by the pump 19, so that the alcohol in the chamber 5*i* is moved to the chamber 5*r* via the chamber 9. Subsequently, only the nozzle inlets 3*i* and 3*t* are opened, air is supplied from the pump 18, and air is sucked by the pump 19, so that the inside of the chamber 9 is dried.

When an operator operates a lever not shown in the figure, the pump blocks 22 and 23 are moved in the direction apart from the biochemical reaction cartridge 1, and the pump nozzles 20 and 21 are disconnected from the nozzle inlets 3 of the cartridge 1. Subsequently, the operator inserts this cartridge 1 in a well-known DNA microarray reading device such as a scanner for measurement and analysis.

In this example, a required number of the liquid sensor units each composed of a light source such as an LED and a light-receiving element such as a photodetector are provided at the lower sides of the respective chambers, which are to be detected, on the table; however, one liquid sensor unit may be used for detection of a plurality of chambers, for example, by relatively moving the liquid sensor unit and the biochemical reaction cartridge. In this case, the states of chambers may be detected at different timings, and this difference is caused by a time required for relative movement of the table and the biochemical reaction cartridge; however, when a method is used in which detection is performed before and after the movement of liquid, any problems may not arise at all, Furthermore, in this example, the liquid sensor unit composed of a light source such as an LED and a light-receiving element such as a photodetector is used; however, after the entire or part of the image of the biochemical reaction cartridge is taken using a two-dimensional sensor such as a CCD, the presence or absence of the liquid or the amount thereof in a chamber of interest may be detected by using well-known image processing.

In addition, in this example, although the presence or absence of the liquid or the amount thereof is detected using an optical detection method, a liquid level sensor using ultrasonic waves may be used, or an electrical detection method may be used in which a voltage is applied between two electrodes provided in a chamber, and the resistance or current therebetween is then measured.

Furthermore, in this example, warning is performed by displaying information indicating the abnormality on the display portion; however, the abnormality may be notified by sound or flashing light.

The present invention is not limited to the above embodiments and various changes and modifications can be made within the spirit and scope of the present invention. Therefore to apprise the public of the scope of the present invention, the following claims are made.

This application claims the benefit of Japanese Application No. 2004-359892 filed Dec. 13, 2004, which is hereby incorporated by reference herein in its entirety.

What is claimed is:

1. A biochemical processing method, comprising the steps of:

providing (i) a biochemical reaction cartridge including, a first chamber and a second chamber, and a flow path communicating between the first chamber and the second chamber, each of the first and second chambers having a transparent bottom, wherein the transparent bottom of one of the chambers is projected in a form of a prism, (ii) a stage on which the biochemical reaction cartridge is placed, (iii) a moving unit for moving liquid via the flow path, (iv) a first detector for detecting the presence of the liquid and/or an amount thereof in the first chamber of the biochemical reaction cartridge placed on the stage, the bottom of the first chamber is configured to face the first detector while the biochemical reaction cartridge is placed on the stage, (v) a second detector for detecting an amount of the liquid in the second chamber of the biochemical reaction cartridge placed on the stage, the bottom of the second chamber is configured to face the second detector while the biochemical reaction cartridge is placed on the stage, and (vi) a determining unit for determining a result of movement of the liquid from information on the liquid in the first and second chambers detected by the first and second detectors;

detecting, before the liquid in the first chamber is moved to the second chamber via the flow path, first liquid information on the presence of the liquid and/or an amount thereof in the first chamber using the first detector and second liquid information on an amount of the liquid in the second chamber using the second detector;

controlling movement of the liquid in the biochemical reaction cartridge by moving the liquid in the first chamber to the second chamber when the first liquid information indicates the presence of the liquid in the first chamber and outputting a signal indicating an abnormality when the first liquid information indicates the absence of the liquid in the first chamber;

detecting, after the liquid in the first chamber is moved to the second chamber via the flow path, third liquid information on the presence of the liquid and/or an amount thereof in the first chamber using the first detector and detecting fourth liquid information on the presence of the liquid and/or an amount thereof in the second chamber using the second detector; and determining whether the movement of the liquid is normally completed or abnormally completed according to the first, second, third, and fourth liquid information, the movement of the liquid is determined as normally completed when the third liquid information indicates the absence of the liquid in the first chamber and the movement of the liquid is determined as abnormally completed when the third liquid information indicates the presence of the liquid in the first chamber.

2. The biochemical processing method according to claim 1, wherein the first, second, third, and fourth liquid information is information indicating the presence or absence of the liquid in the chambers.

3. The biochemical processing method according to claim 1, wherein the first and the third liquid information is information indicating the presence or absence of the liquid in the first chamber, and the second and the fourth liquid information is information indicating the amount of the liquid in the second chamber.

4. The biochemical processing method according to claim 1, wherein when the movement of the liquid is determined as abnormal, the liquid in the first chamber is again moved to the second chamber, and the presence or absence of the liquid in the first chamber is detected as a fifth liquid information, when the fifth liquid information indicates the absence of the liquid in the first chamber, the amount of the liquid in the second chamber is detected as a sixth liquid information, and the sixth liquid information is compared with the fourth liquid information, when the amount of the liquid obtained from the sixth liquid information is more than the amount of the liquid obtained from the fourth liquid information, it is determined that the movement of the liquid is normally completed, and when the amount of the liquid obtained from the sixth liquid information is equal to or less than the amount of the liquid obtained from the fourth liquid information, the movement of the liquid is determined as abnormal.

5. The biochemical processing method according to claim 1, wherein when the movement of the liquid is determined as normal, the fourth liquid information is compared with the second liquid information, when the amount of the liquid obtained from the fourth liquid information is more than the amount of the liquid obtained from the second liquid information, it is determined that the movement of the liquid is normally completed, and when the amount of the liquid obtained from the fourth liquid information is equal to or less than the amount of the liquid obtained from the second liquid information, the movement of the liquid is determined as abnormal.

6. A biochemical processing method, comprising the steps of:
providing (i) a biochemical reaction cartridge including, a first chamber and a second chamber, and a flow path communicating between the first chamber and the second chamber, each of the first and second chambers having a transparent bottom, wherein the transparent bottom of one of the chambers is projected in a form of a prism, (ii) a stage on which the biochemical reaction cartridge is placed, (iii) a moving unit for moving liquid via the flow path, (iv) a first detector for detecting the presence of the liquid and/or an amount thereof in the first chamber of the biochemical reaction cartridge placed on the stage, the bottom of the first chamber is configured to face the first detector while the biochemical reaction cartridge is placed on the stage, (v) a second detector for detecting an amount of the liquid in the second chamber of the biochemical reaction cartridge placed on the stage, the bottom of the second chamber is configured to face the second detector while the biochemical reaction cartridge is placed on the stage, and (vi) a determining unit for determining a result of movement of the liquid from information on the liquid in the first and second chambers detected by the first and second detectors;
detecting first liquid information on an amount of the liquid in the first chamber using the first detector;
detecting second liquid information on an amount of the liquid in the second chamber using the second detector; and
controlling movement of the liquid in the biochemical reaction cartridge according to the first and second liquid information.

\* \* \* \* \*